(12) United States Patent
Bagchi et al.

(10) Patent No.: US 10,022,349 B2
(45) Date of Patent: Jul. 17, 2018

(54) CADOTRIL PARTICLES

(71) Applicant: Johnson & Johnson Consumer Inc., Skillman, NJ (US)

(72) Inventors: Saumitra Bagchi, Princeton, NJ (US); Murali K. Vuppala, Collegeville, PA (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 30 days.

(21) Appl. No.: 14/926,533

(22) Filed: Oct. 29, 2015

(65) Prior Publication Data

US 2016/0120834 A1    May 5, 2016

Related U.S. Application Data

(60) Provisional application No. 62/069,902, filed on Oct. 29, 2014.

(51) Int. Cl.
| A61K 31/216 | (2006.01) |
| A61K 9/20 | (2006.01) |
| A61K 47/08 | (2006.01) |
| A61K 9/00 | (2006.01) |
| A61K 9/10 | (2006.01) |
| A61K 9/14 | (2006.01) |

(52) U.S. Cl.
CPC ......... *A61K 31/216* (2013.01); *A61K 9/0056* (2013.01); *A61K 9/10* (2013.01); *A61K 9/145* (2013.01); *A61K 9/2013* (2013.01); *A61K 9/2077* (2013.01); *A61K 47/08* (2013.01)

(58) Field of Classification Search
CPC ........ A61K 9/0056; A61K 9/10; A61K 9/145; A61K 9/2013; A61K 1/216; A61K 47/08
See application file for complete search history.

(56) References Cited

U.S. PATENT DOCUMENTS

| 4,513,009 A | 4/1985 | Roques et al. |
| 4,851,226 A | 7/1989 | Julian et al. |
| 5,075,114 A | 12/1991 | Roche |
| 5,136,076 A | 8/1992 | Duhamel et al. |
| 5,208,255 A | 5/1993 | Duhamel et al. |
| 5,250,236 A * | 10/1993 | Gasco ............... A61K 9/5123 264/4.3 |
| 5,296,509 A | 3/1994 | Duhamel et al. |
| 5,331,008 A | 7/1994 | Duhamel et al. |
| 5,489,436 A | 2/1996 | Hoy et al. |
| 6,919,093 B2 | 7/2005 | Lecomte et al. |
| 8,222,294 B2 | 7/2012 | Schwartz et al. |
| 8,318,203 B2 | 11/2012 | Schwartz et al. |

(Continued)

FOREIGN PATENT DOCUMENTS

| CN | 101264065 A | 9/2008 |
| CN | 101103960 B | 12/2010 |

(Continued)

OTHER PUBLICATIONS

Matheson AJ, Noble S (Apr. 2000). "Racecadotril". Drugs 59 (4): 829-35; discussion 836-7.

(Continued)

*Primary Examiner* — Jianfeng Song
(74) *Attorney, Agent, or Firm* — Laura A. Donnelly

(57) ABSTRACT

Cadotril particles suitable for solid or liquid dosage forms are the subject of this application.

4 Claims, 2 Drawing Sheets

(56) References Cited

U.S. PATENT DOCUMENTS

| | | | |
|---|---|---|---|
| 2002/0028248 A1 | 3/2002 | Tsukada et al. | |
| 2011/0070304 A1* | 3/2011 | Kriksunov | A61J 3/10 424/468 |
| 2013/0017239 A1* | 1/2013 | Viladot Petit | A61K 8/0283 424/401 |
| 2013/0331423 A1 | 12/2013 | Julien et al. | |
| 2014/0005261 A1 | 1/2014 | Lee | |
| 2014/0005262 A1 | 1/2014 | Lee | |
| 2014/0213653 A1 | 7/2014 | Bagchi et al. | |

FOREIGN PATENT DOCUMENTS

| | | |
|---|---|---|
| CN | 102133186 A | 7/2011 |
| CN | 102327234 A | 1/2012 |
| EP | 2749270 A1 | 7/2014 |
| IN | 200601652 I3 | 7/2008 |
| IN | 200800884 I3 | 11/2011 |
| IN | 2011011912 I1 | 10/2012 |
| IN | 201101274I1 A1 | 11/2012 |
| IN | 201101275 I1 | 11/2012 |
| WO | WO 2001/097803 A1 | 12/2001 |
| WO | WO 2014/005032 A1 | 1/2014 |

OTHER PUBLICATIONS (2001) "Racecadotril: an Antidiarrheal Suitable for Use in Infants and Young Children". Drug Ther Perspect 17 (8): 1-5.
Salazar-Lindo E, Santisteban-Ponce J, Chea-Woo E, Gutierrez M (2000). "Racecadotril in the treatment of acute watery diarrhea in children". N. Engl. J. Med. 343 (7): 463-7.
Spillantini MG, Geppetti P, Fanciullacci M, Michelacci S, Lecomte JM, Sicuteri F (Jun. 1986). "In vivo 'enkephalinase' inhibition by acetorphan in human plasma and CSF". European Journal of Pharmacology 125 (1): 147-50.
Leiberman et al., Pharmaceutical Dosage Forms—Tablets, vol. 2, 2.sup.nd ed., Marcel Dekker Inc., 1990, pp. 213-217, 327-329.
USP 24 (United States Pharmacopeia 24, United States Pharmacopeia Convention, Inc., Rockville, MD). pp. 1940-1943.
Diarrhoea: why children are still dying and what can be done, The United Nations Children's Fund, World Health Organization, 2009.
Diarrhoeal Disease Fact Sheet N°330, World Health Organization, Apr. 2013.
Dupont, H.L., Acute infectious diarrhea in immunocompetent adults, New England Journal of Medicine, 2014, 370:1532-40.
Allen S.J., et al., Probiotics for treating acute infectious diarrhoea (Review), Cochrane Database of Systematic Reviews 2010, Issue 11. Art. No. CD003048. DOI: 10.1002/14651858.CD003048.pub3.
Schwartz J.C., Int. Antimicrob. Agents, 2000, 14, 81.
Lecomte et al., Int. J. Antimicrob. Agents, 2000, 14, 81.
International Search Report for PCT/US2015/058007 dated Dec. 21, 2015.

* cited by examiner

CADOTRIL PARTICLES

This application claims priority of the benefits of the filing of U.S. Provisional Application Ser. No. 62/069,902, filed Oct. 29, 2014, the contents of each of which are hereby incorporated by reference in their entirety.

FIELD OF THE INVENTION

The present invention relates to cadotril particles. The invention also relates to methods of manufacturing the cadotril particles; dosage forms containing the cadotril particles; methods of manufacturing the dosage forms; and methods of treatment using the dosage forms.

BACKGROUND OF THE INVENTION

Diarrhea or diarrhoea is defined by the World Health Organization as a condition of having at least three loose or liquid bowel movements each day or as having more stool than is normal for that person.[1] It often lasts for a few days and can result in dehydration due to fluid loss.

[1] See Diarrhoeal Disease Fact Sheet N°330, World Health Organization, April 2013.

The most common cause of diarrhea is an infection of the intestines due to a virus, bacteria, or parasite, a condition known as gastroenteritis. These infections are often acquired from food or water that has been contaminated by stool, or directly from another person who is infected. A number of non-infectious causes may also result in diarrhea including: hyperthyroidism, lactose intolerance, inflammatory bowel disease, a number of medications, and irritable bowel syndrome among others.

Prevention of infectious diarrhea is by improved sanitation, clean drinking water, and hand washing. Oral rehydration solution (ORS), which is clean water with modest amounts of salt and sugar, along with zinc tablets are often employed. In those with severe dehydration, intravenous fluids may be required.

About 1.7 to 5 billion cases of diarrhea occur per year.[2] It is most common in developing countries were young children get diarrhea on average three times a year. Worldwide, as of 2012, it is the second most common cause of death in children less than five (0.76 million or 11%).[3] Frequent episodes of diarrhea are also a common cause of malnutrition and the most common cause in those less than five years of age. Other long term problems that can result include poor physical and intellectual development.

[2] See Diarrhoea: why children are still dying and what can be done, The United Nations Children's Fund, World Health Organization, 2009.
[3] See Diarrhoeal Disease Fact Sheet N°330, World Health Organization, April 2013.

Chronic diarrhea can be the part of the presentations of a number of chronic medical conditions affecting the intestine. Common causes include ulcerative colitis, Crohn's disease, microscopic colitis, celiac disease, irritable bowel syndrome and bile acid malabsorption.

While antibiotics are beneficial in certain types of acute diarrhea, they are usually not used except in specific situations as some bacteria develop antibiotic resistance. Antibiotics themselves can also cause diarrhea, and antibiotic-associated diarrhea is the most common adverse effect associated with treatment using general antibiotics.

Anti-motility agents like loperamide are also effective at reducing the number of stools but not the duration of disease.[4]

[4] See Dupont, H. L., Acute infectious diarrhea in immunocompetent adults, New England Journal of Medicine, 2014, 370:1532-40.

Probiotics are "friendly" bacteria that have proven beneficial in the treatment of diarrhea.[5]

[5] See Allen S. J., et al., Probiotics for treating acute infectious diarrhoea (Review), Cochrane Database of Systematic Reviews 2010, Issue 11. Art. No.: CD003048. DOI: 10.1002/14651858.CD003048.pub3.

Racecadotril (shown below), also known as acetorphan or (RS)-benzyl N-[3-(acetylthio)-2-benzylpropanoyl]glycinate, is an antidiarrheal drug which acts as a peripherally acting enkephalinase inhibitor. Unlike other medications used to treat diarrhea, which reduce intestinal motility, racecadotril has an antisecretory effect, i.e., it reduces the secretion of water and electrolytes into the intestine. Racecadotril exhibits an original intestinal antisecretory action, by protecting endogenous enkephalines against the degradation thereof. By improving the biological activity of these neuropeptides at the delta opiate receptors, racecadotril reduces the hydroelectric flows in the intestinal lumen, which flows are otherwise increased in diarrheal diseases of various origins. Racecadotril is selective in that the intestinal hypersecretion (or reduced electrolyte reabsorption) which characterizes diarrhoea and is responsible for severe states of dehydration is greatly reduced without altering the transit.[6] This model contributes to the particularly beneficial properties of racecadotril, as has already been shown in clinical trials and post-marketing study.[7]

[6] Matheson A. J., et al., Drugs 2000, 59, 829; Schwartz J. C., Int. Antimicrob. Agents, 2000, 14, 81.
[7] Lecomte et al., Int. J. Antimicrob. Agents, 2000, 14, 81.

In clinical trials as well as in standard practice, racecadotril is generally administered in 100 mg capsules, taken three times a day, in order to ensure complete inhibition of the targeted peptidase throughout the day without interruption. A twice a day (b.i.d.) tablet has also been studied.

Racecadotril is sold in the market in a number of countries under the tradename HIDRASEC® (trademark of SmithKline Beecham) and TIORFAN® (trademark of Societe Civile de Recherche Bioprojet). One marketed form is a dry powder filled into a hard gelatin capsule.

It is desirable to have additional formulations of racecadotril.

Dexecadotril (shown below), also known as R-acetorphan or N—[(R)-2-Benzyl-3-(acetylthio)propionyl]glycine benzyl ester; N—[(R)-2-[(Acetylthio)methyl]-1-oxo-3-phenylpropyl]glycine benzyl ester is the R enantiomer of racecadotril.

Ecadotril (shown below), also known as S-acetorphan or N—[(S)-2-[(Acetylthio)methyl]-1-oxo-3-phenylpropyl]glycinebenzyl ester is the S enantiomer of racecadotril.

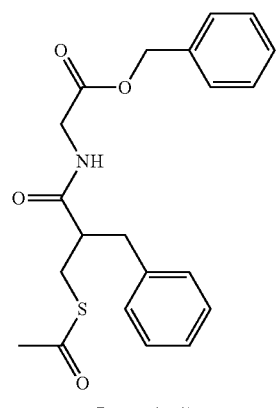

Racecadotril

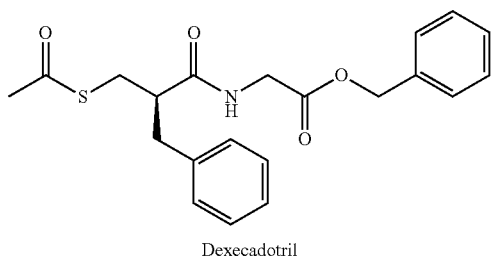

Dexecadotril

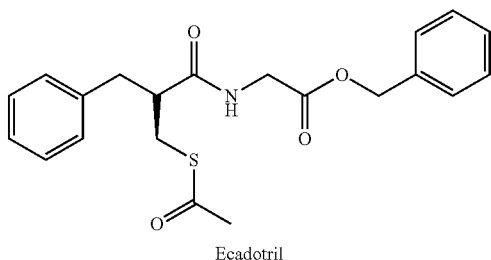

Ecadotril

Throughout the disclosure "cadotril" will be used to include racecadotril, dexecadotril and/or ecadotril.

Racecadotril is a class II drug (as per Biopharmaceutical Classification System) with poor aqueous solubility and dissolution rate limited absorption. Racecadotril undergoes hydrolysis when it comes into contact with water. There are two major pairs of hydrolysis products, i.e., benzyl alcohol and EP Impurity C and thioacetic acid and EP Impurity G. Thiorphan, which is a product of the hydrolysis reaction, is not a major degradation product. Thiorphan (shown below) is the active metabolite of racecadotril, which exerts the bulk of its inhibitory actions on enkephalinase.

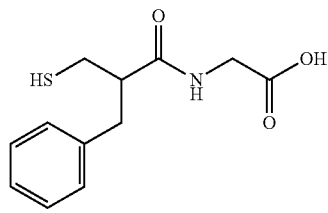 [SMILES: O=C(O)CNC(=O)C(CS)Cc1ccccc1]

U.S. Pat. No. 4,513,009 to Bioprojet discloses racecadotril and some of its therapeutic applications.

U.S. Pat. Nos. 5,331,008; 5,296,509; 5,208,255; and 5,136,076 to Bioprojet disclose enantiomeric forms of racecadotril.

U.S. Pat. No. 6,919,093 to Bioprojet discloses a dry powder racecadotril formulation that comprises coated granules and specified excipients.

U.S. Pat. No. 8,222,294 to Bioprojet discloses a combination that comprises racecadotril or dexecadotril with ondansetron or granisetron.

U.S. Pat. No. 8,318,203 to Bioprojet discloses a racecadotril tablet that comprises a coated core and specified excipients.

U.S. Application No. 20130331423 to Bioprojet discloses an aqueous suspension that comprises racecadotril.

WO2001097803 to GlaxoSmithKline discloses a granulate formulation comprising racecadotril and specified excipients.

U.S. Application No. 20020028248 to Tsukada et al. discloses rapid-release microdispersible preparation containing ecadotril.

CN102133186 to Hainan Meida Pharmaceutical Co. discloses a liposome racecadotril solid preparation that comprises specified ingredients in specified relative weight ratios.

CN101103960 to Hainan Shengke Life Scientific Research Institute and CN102327234 to Hainan Honz Pharmaceutical Co., Ltd. each disclose racecadotril containing dry suspensions that comprises specified ingredients.

CN101264065 to Yancheng Suhai Pharmaceutical Co., Ltd. discloses a racecadotril dropping pill that comprises specified ingredients in specified weight ratios.

IN20110127511, IN20110127411 and IN201101191211 to Akums disclose pharmaceutical formulations that comprise (1) racecadotril and (2) ofloxacin and/or ornidazole.

IN20080088413 to Torrent Pharmaceuticals Limited discloses a resinate complex that comprises racecadotril.

IN20060165213 to Torrent Pharmaceuticals Limited discloses a taste-masked composition that comprises particles comprising racecadotril and a low melting excipient. The composition is prepared by dispersing racecadotril in a melt; cooling the dispersion at room temperature to form a solidified mass; and milling the solidified mass to obtain racecadotril particles.

U.S. Application No. 20140005262 to McNeil-PPC, Inc. discloses a composition that comprises racecadotril, at least one surfactant and a lipid.

U.S. Application No. 20140005261 to McNeil-PPC, Inc. discloses a liquid composition that comprises racecadotril and cyclodextrin.

EP2749270 discloses a dispersible tablet comprising racecadotril coated with an acrylic acid polymer or a cellulose polymer by a wet granulation method.

There continues to be a need for cadotril products having the attributes discussed above.

SUMMARY OF THE INVENTION

The art recognizes that cadotrils such as racecadotril are difficult to formulate into compositions because of their hydrophobic and chemically unstable nature. In addition, cadotrils such as racecadotril are known to have a bitter taste. There is thus a need for alternative compositions of cadotrils such as racecadotril. The present inventors have found that various types of formulations may be prepared using the cadotril particles of the invention.

The present invention relates to cadotril particles. The cadotril particles exhibit reduced degradation in various environments. The cadotril particles also taste mask the bitterness often experienced when ingesting dosage forms containing cadotril.

The invention also relates to methods of manufacturing the cadotril particles; dosage forms containing the cadotril particles; methods of manufacturing the dosage forms; and methods of treatment using the dosage forms.

In accordance with an embodiment of the invention, cadotril particles are prepared as follows:

cadotril and wax are melted while mixing;

the molten cadotril/wax mixture is dispersed in hot water;

the hot dispersion is transferred into another container containing ambient/cold water;

the dispersed droplets of cadotril/wax congeal as a result of the rapid drop in temperature and form fine/spherical particles;

the fine/spherical particles are filtered and dried.

The process of the invention can be used to manufacture cadotril particles that range in size from about 50 microns to about 600 microns, preferably from about 170 to about 300 microns, more preferably about 250 microns. Table 1 below shows the results of measurement of the cadotril particles prepared in accordance with an embodiment of the invention (see Example 1), where the material was screened and the amount of material that stayed on the screen was assessed. As can be seen, most of the particles in Table 1 are 250 microns or larger.

TABLE 1

| Mesh # | um | Initial Weight (g) | Final Weight (g) | Net Weight (g) | % Retained |
|---|---|---|---|---|---|
| 30 | 600 | 42.55 | 43.04 | 0.49 | 9.86% |
| 60 | 250 | 35.69 | 39.22 | 3.53 | 71.03% |
| 80 | 180 | 34.52 | 34.97 | 0.45 | 9.05% |
| 100 | 150 | 32.21 | 32.49 | 0.28 | 5.63% |
| 170 | 90 | 33.7 | 33.86 | 0.16 | 3.22% |
| 200 | 75 | 33.19 | 33.21 | 0.02 | 0.40% |
| Base | 0 | 158.74 | 158.78 | 0.04 | 0.80% |
| Total | | | | 4.97 | 100% |

The process of the invention can be used to manufacture cadotril particles with a narrow particle size range. Mixing speed; congealing; nozzle size can be modified to vary particle sizes.

The process of the invention can be used to manufacture cadotril particles for use in various pediatric and adult dosage forms. For example, the process of the invention can be used to manufacture cadotril particles for use in dosage forms including, but not limited to, caplets, capsules, films, granules, powders, suspensions, tablets and other dosage forms suitable for oral administration.

The dosage forms can be, e.g., chewable, effervescent, orally disintegrating or swallowable.

In a preferred embodiment, the cadotril particles can be utilized in liquid dosage forms such as suspensions. According to this embodiment, the particles may or may not be dried prior to incorporation into a suspension vehicle.

In a preferred embodiment, the suspension is prepared as follows:

cadotril and wax are melted while mixing;

the molten cadotril/wax mixture is dispersed in hot water or hot water containing pharmaceutically preferred suspending agents (e.g., xanthan gum);

the hot dispersion is transferred into another container containing ambient/cold suspension vehicle;

the dispersed droplets of cadotril/wax congeal as a result of the rapid drop in temperature and form fine/spherical particles;

the suspension is completed by addition of the excipients, sweeteners, preservatives, and/or flavors.

According to another preferred embodiment, the suspension is prepared by separating the congealed cadotril/wax particles, drying and incorporating into a suspension by combining with excipients and water.

Waxes and/or lipids with high melting points (e.g., about 60° to about 80° C. as measured using, e.g., differential scanning calorimetry, can be used in accordance with the invention. "Wax" is being used throughout this specification to include waxes and/or lipids that may be used in accordance with the invention. Examples include carnauba wax, glyceryl behenate, glyceryl tripalmitate, glycerol tristearate and microcrystalline wax. Additional examples and melting points are set forth in Table 2 below.

TABLE 2

| Excipients | Melting Point (° C.) |
|---|---|
| cocoa butter | 35-37 |
| hydrogenated palm kernel oil | 30 |
| hydrogenated cottonseed oil | 50-60 |
| hydrogenated sunflower oil | 30 |
| hydrogenated soybean oil | 30 |
| glyceryl behenate | 70-75 |
| glyceryl palmitostearate | 60-70 |
| glyceryl monostearate | 50-60 |
| glyceryl tristearate | 72-75 |
| glyceryl trilaurylate | 47 |
| GlycoWax-932 | 58-64 |
| lauroyl macrogol-32 glycerides | 44 |
| stearoyl macrogol-32 glycerides | 50 |
| carnauba wax | 82 |
| spermaceti wax | 46-50 |
| beeswax | 62-64 |
| candelilla wax | 68-72 |
| shellac wax | |
| microcrystalline wax | 60-80 |
| paraffin wax | 37 |
| Chocolate | 30-35 |

According to another preferred embodiment, the cadotril particles can be incorporated into a tablet by combining with excipients.

Suitable fillers include, but are not limited to, carbohydrates (as discussed herein) and water insoluble plastically deforming materials (e.g., microcrystalline cellulose or other cellulosic derivatives), and mixtures thereof.

Suitable adsorbents include, but are not limited to, water-insoluble adsorbents such as dicalcium phosphate, tricalcium phosphate, silicified microcrystalline cellulose (e.g., such as distributed under the PROSOLV brand (PenWest Pharmaceuticals, Patterson, N.Y.)), magnesium aluminometasilicate (e.g., such as distributed under the NEUSILIN brand (Fuji Chemical Industries (USA) Inc., Robbinsville, N.J.)), clays, silicas, bentonite, zeolites, magnesium silicates, hydrotalcite, veegum, and mixtures thereof.

Suitable disintegrants include, but are not limited to, sodium starch glycolate, cross-linked polyvinylpyrrolidone, cross-linked carboxymethylcellulose, starches, microcrystalline cellulose, and mixtures thereof.

Suitable lubricants include, but are not limited to, long chain fatty acids and their salts, such as magnesium stearate and stearic acid, talc, glycerides waxes, and mixtures thereof.

Suitable glidants include, but are not limited to, colloidal silicon dioxide.

Examples of sweeteners include, but are not limited to, synthetic or natural sugars; artificial sweeteners such as saccharin, sodium saccharin, aspartame, acesulfame, thaumatin, glycyrrhizin, sucralose, dihydrochalcone, alitame, miraculin, monellin, and stevside; sugar alcohols such as sorbitol, mannitol, glycerol, lactitol, maltitol, and xylitol; sugars extracted from sugar cane and sugar beet (sucrose), dextrose (also called glucose), fructose (also called laevulose), and lactose (also called milk sugar); isomalt, salts thereof, and mixtures thereof.

Examples of superdisintegrants include, but are not limited to, croscarmellose sodium, sodium starch glycolate and cross-linked povidone (crospovidone). In one embodiment the tablet contains up to about 5% by weight of such superdisintegrant.

Examples of flavors and aromatics include, but are not limited to, essential oils including distillations, solvent extractions, or cold expressions of chopped flowers, leaves, peel or pulped whole fruit containing mixtures of alcohols, esters, aldehydes and lactones; essences including either diluted solutions of essential oils, or mixtures of synthetic chemicals blended to match the natural flavor of the fruit (e.g., strawberry, raspberry and black currant); artificial and natural flavors of brews and liquors, e.g., cognac, whisky, rum, gin, sherry, port, and wine; tobacco, coffee, tea, cocoa, and mint; fruit juices including expelled juice from washed, scrubbed fruits such as lemon, orange, and lime; spear mint, pepper mint, wintergreen, cinnamon, cacoe/cocoa, vanilla, liquorice, menthol, eucalyptus, aniseeds nuts (e.g., peanuts, coconuts, hazelnuts, chestnuts, walnuts, colanuts), almonds, raisins; and powder, flour, or vegetable material parts including tobacco plant parts, e.g., genus *Nicotiana*, in amounts not contributing significantly to the level of nicotine, and ginger.

Examples of antioxidants include, but are not limited to, tocopherols, ascorbic acid, sodium pyrosulfite, butylhydroxytoluene, butylated hydroxyanisole, edetic acid, and edetate salts, and mixtures thereof.

Examples of preservatives include, but are not limited to, citric acid, tartaric acid, lactic acid, malic acid, acetic acid, benzoic acid, and sorbic acid, and mixtures thereof.

Examples of texture enhancers include, but are not limited to, pectin, polyethylene oxide, and carrageenan, and mixtures thereof. In one embodiment, texture enhancers are used at levels of from about 0.1% to about 10% percent by weight.

If the pharmaceutically active agent has an objectionable taste, the pharmaceutically active agent may be coated with a taste masking coating, as known in the art. Examples of suitable taste masking coatings are described in U.S. Pat. Nos. 4,851,226, 5,075,114, and 5,489,436. Commercially available taste masked pharmaceutically active agents may also be employed. For example, acetaminophen particles, which are encapsulated with ethylcellulose or other polymers by a coacervation process, may be used in the present invention. Coacervation-encapsulated acetaminophen may be purchased commercially from Eurand America, Inc. (Vandalia, Ohio) or from Circa Inc. (Dayton, Ohio).

Orally Disintegrating Tablet

In one embodiment, the tablet is designed to disintegrate in the mouth when placed on the tongue in less than about 60 seconds, e.g. less than about 45 seconds, e.g. less than about 30 seconds, e.g. less than about 15 seconds.

In one embodiment, the tablet meets the criteria for Orally Disintegrating Tablets (ODTs) as defined by the draft Food and Drug Administration guidance, as published in April, 2007. In one embodiment, the tablet meets a two-fold definition for orally disintegrating tablets including the following criteria: 1) that the solid tablet is one which contains medicinal substances and which disintegrates rapidly, usually within a matter of seconds, when placed upon the tongue and 2) be considered a solid oral preparation that disintegrates rapidly in the oral cavity, with an in vitro disintegration time of approximately 30 seconds or less, when based on the United States Pharmacopeia (USP) disintegration test method for the specific medicinal substance or substances.

Hardness/Density of Tablet Shape/Tablet

In one embodiment, the tablet is prepared such that the tablet is relatively soft (e.g., capable of disintegrating in the mouth or being chewed). In one embodiment, the hardness of the tablet is preferably less than about 3 kiloponds per square centimeter (kp/cm2) (e.g., less than about 2 kp/cm2, such as less than about 1 kp/cm2). Hardness is a term used in the art to describe the diametral breaking strength as measured by conventional pharmaceutical hardness testing equipment, such as a Schleuniger Hardness Tester. In order to compare values across different size tablets, the breaking strength must be normalized for the area of the break. This normalized value, expressed in kp/cm2, is sometimes referred in the art as tablet tensile strength. A general discussion of tablet hardness testing is found in Leiberman et al., Pharmaceutical Dosage Forms—Tablets, Volume 2, 2.sup.nd ed., Marcel Dekker Inc., 1990, pp. 213-217, 327-329.

Use of Tablet

The tablets may be used as swallowable, chewable, or orally disintegrating tablets to administer the pharmaceutically active agent.

In one embodiment, the present invention features a method of treating an ailment, the method including orally administering the above-described tablet wherein the tablet includes an amount of the pharmaceutically active agent effective to treat the ailment. In this embodiment, the "unit dose" is typically accompanied by dosing directions, which instruct the patient to take an amount of the pharmaceutically active agent that may be a multiple of the unit dose depending on, e.g., the age or weight of the patient. Typically the unit dose volume will contain an amount of pharmaceutically active agent that is therapeutically effective for the smallest patient. For example, suitable unit dose volumes may include one tablet.

The tablet shape may have one of a variety of different shapes. For example, the tablet shape may be shaped as a polyhedron, such as a cube, pyramid, prism, or the like; or may have the geometry of a space figure with some non-flat faces, such as a cone, truncated cone, triangle, cylinder, sphere, torus, or the like. In certain embodiments, a tablet shape has one or more major faces. For example, the tablet shape surface typically has opposing upper and lower faces formed by contact with the upper and lower forming tool faces (e.g., die punches) in the compaction machine. In such embodiments, the tablet shape surface typically further includes a "belly-band" located between the upper and lower faces, and formed by contact with the die walls in the compaction machine. A tablet shape/tablet may also be a multilayer. Applicants have found that sharp edges in the tooling used to make the tablets can cause arcing, and thus more rounded edges may be needed.

Sachet Composition

In one embodiment the particles of the present invention can be incorporated into a directly orally administered powder, such as a sachet composition. The blend materials which may be incorporated into a tablet formulation may also be utilized in a powder formulation. In another embodiment, the powder formulation is intended for reconstitution into a liquid.

The particles of the invention assist in the avoidance of chemical incompatability between racecadotril and excipients.

The process of the invention can also be used to manufacture cadotril particles for use in immediate release or in sustained release dosage forms. In one embodiment, the immediate release cadotril particles may be incorporated with sustained release cadotril particles to create a dosage form with immediate release and sustained release characteristics.

A preferred ratio of cadotril/wax for an immediate release dosage form is from about 50:50 to about 95:5. A more preferred ratio of cadotril/wax for an immediate release dosage form is 85:15. A preferred ratio of cadotril/wax for a sustained release dosage form is from about 5:95 to about 30:70.

In another embodiment, the cadotril particles may be combined with one or more additional active ingredient(s). E.g., suitable anti-gas agents include, but are not limited to simethiconeSuitable additional antidiarrheal agents include, but are not limited to loperamide Other features and advantages of the present invention will be apparent from the detailed description of the invention and from the claims.

DETAILED DESCRIPTION OF THE INVENTION

Figure 1:
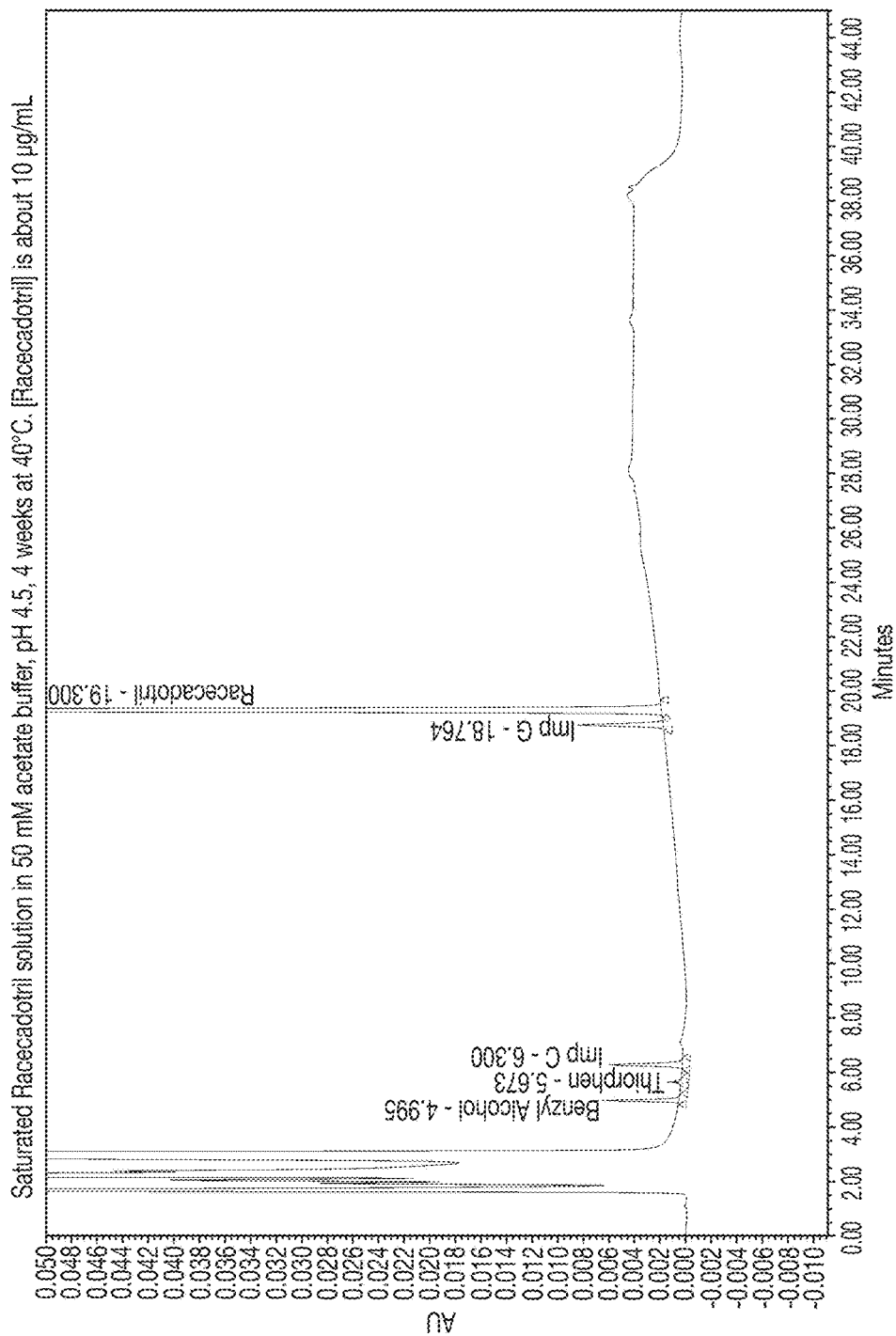
FIG. 1 is a graph showing the degradation profile for racecadotril in a cadotril particle of the invention prepared in accordance with Example 1.

It is believed that one skilled in the art can, based upon the description herein, utilize the present invention to its fullest extent. The following specific embodiments are to be construed as merely illustrative, and not as limiting the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference. As used herein, all percentages are by weight unless otherwise specified. In addition, all ranges set forth herein are meant to include any combinations of values between the two endpoints, inclusively.

Definitions

By "delayed release," it is meant that, after administration, there is at least one period of time when an active ingredient is not being released from the dosage form, i.e., the release of the active ingredient(s) occurs at a time other than immediately following administration.

As used herein, "dissolution medium" shall mean any suitable liquid environment in which the dosage form of the present invention can be dissolved, such as, for example, the in vitro dissolution media used for testing of the product, or gastro-intestinal fluids. Suitable in vitro dissolution media used for testing the dissolution of the active ingredient or ingredients from the suspension dosage form of the present invention include those described in the United States Pharmacopeia.

A "dosage", "dosage form" or "dose" as used herein means the amount of a pharmaceutical formulation comprising therapeutically active agent(s) administered at a time. "Dosage", "dosage form" or "dose" includes administration of one or more units of pharmaceutical formulation administered at the same time. In one embodiment, the dosage form is a tablet. In one embodiment the dosage form is a multilayer tablet. In the embodiment comprising a multilayer tablet, one layer may comprise an immediate release portion and another layer may comprise an extended release portion. In the embodiment comprising a multilayer tablet, one layer may comprise the cadotril particles, and another layer may comprise an immediate release form of cadotril and/or a second active ingredient. In one embodiment the dosage form comprising cadotril particles is a liquid filled soft-gel.

"Enteric" shall mean being able to be dissolved at a pH of greater than about 5.0 or greater than about 5.5 or greater than about 6.0 or that which is found in the intestine.

By "extended release," it is meant that, after administration, an active ingredient is released from the dosage form in a substantially continuous, regulated manner, and the time for complete release, i.e., depletion, of the active ingredient from the dosage form is longer than that associated with an immediate release dosage form of the same. Types of extended release include controlled, sustained, prolonged, zero-order, first-order, pulsatile, and the like.

As used herein, "immediate release" means that the dissolution characteristics of at least one active ingredient meet USP specifications for immediate release tablets containing that active ingredient. An active ingredient having an immediate release property may be dissolved in the gastrointestinal contents, with no intention of delaying or prolonging the dissolution of the active ingredient.

"Liquid dosage forms" may nonexclusively include suspensions or elixirs, wherein one or more of the active ingredients is dissolved, partially dissolved or in an undissolved or suspended state.

As used herein, "modified release" shall apply to the altered release or dissolution of an active ingredient in a dissolution medium, such as gastrointestinal fluids. Types of modified release include: 1) extended release; or 2) delayed release. In general, modified release dosage forms are formulated to make the active ingredient(s) available over an extended period of time after ingestion, which thereby allows for a reduction in dosing frequency compared to the dosing of the same active ingredient(s) in a conventional dosage form. Modified release dosage forms also permit the use of active ingredient combinations wherein the duration of one active ingredient may differ from the duration of another active ingredient.

As used herein, a drug "release rate" refers to the quantity of drug released from a dosage form per unit time, e.g., milligrams of drug released per hour (mg/hr). Drug release rates are calculated under in vitro dosage form dissolution testing conditions known in the art. As used herein, a drug release rate obtained at a specified time "following administration" refers to the in vitro drug release rate obtained at the specified time following commencement of an appropriate dissolution test, e.g., those set forth in USP 24 (United States Pharmacopeia 24, United States Pharmacopeia Convention, Inc., Rockville, Md.).

"Semipermeable," as used herein, shall mean that water can pass through, and other molecules, including salts and the active ingredients described herein, are allowed to slowly diffuse through such a membrane when the membrane is in contact with an appropriate dissolution medium, e.g., gastro-intestinal fluids or in-vitro dissolution media.

"Solid dosage forms" shall mean dosage forms which are substantially solid at room temperature and have a density of at least about 0.5 g/cc. Solid dosage forms may non exclusively include, agglomerated tablets, capsule-like medicaments, powder or granule filled capsules, powder or granule filled sachets, compressed tablets, coated tablets, chewable dosage forms, and fast-dissolving dosage forms.

As used herein, "substantially coated" with regard to particles shall mean that less than about 20%, e.g., less than about 15%, or less than about 1.0% of the surface area of the particle is exposed, e.g., not covered, with a desired coating. As used herein, the term "substantially covers" or "substantially continuous" when used to describe a coating means that the coating is generally continuous and generally covers the entire surface of the core or underlying layer, so that little to none of the active ingredient or underlying layer is exposed. The coatings which are applied to the particles can be layered wherein each layer is prepared in an aqueous (water based) or organic solvent system and added in succession until the desired coating level is achieved.

"Therapeutic effect," as used herein, shall mean any effect or action of an active ingredient intended to diagnose, treat, cure, mitigate, or prevent disease, or affect the structure or any function of the body.

The present invention relates to chemically stable cadotril particles, such as racecadotril, dexecadotril and ecadotril particles, the process for the preparation thereof, and the use thereof in pharmaceutical formulations.

The present invention also includes a method for treating a subject experiencing diarrhea comprising the step of orally administering to the subject a pharmaceutical formulation comprising cadotril particles.

Racecadotril, dexecadotril and ecadotril are enkephalinase inhibitors with unique intestinal antisecretory activity. The compounds are insoluble in water.

Their bitter taste and degradation profile have rendered formulation challenging. For example, a difficulty in preparing stable suspensions of racecadotril is the risk of hydrolysis of this compound which bears an ester group and can be easily hydrolyzed into easily oxidizable and less active compounds.

The present inventors have now discovered that the cadotril particles of the invention can fulfil the above requirements.

As The cadotril particles of the invention can be employed in varying dosage forms.

A typical aqueous suspension of the invention may comprise water-soluble high intensity sweeteners and sugar sweeteners. Examples of suitable high intensity sweeteners include, but are not limited to, sucralose, aspartame, saccharin, acesulfame, cyclamate, and pharmaceutically acceptable salts and combinations thereof. The amount of high intensity sweetener used in the suspension will vary depending on the degree of sweetening desired for the particular suspension. Generally, the amount of high intensity sweeteners used in the suspension may vary from in the range of 0 to about 5 grams per 100 mL of suspension. In embodiments employing a high intensity sweetener, such as sucralose, aspartame, acesulfame, saccharin, and pharmaceutically acceptable salts thereof, the level of high intensity sweetener is from 0 to about 1 gram per 100 mL of suspension, a useful level is from about 0 to about 0.5 gram per 100 mL of suspension.

The suspension can be buffered using pH adjusting agents to maintain the pH of the suspension in the desired pH range. Suitable pH-adjusting agents may be present in the suspension in amounts sufficient to provide the desired degree of pH buffering. The pH-adjusting agents will typically be present in the range of from about 0 to about 1 gram per 100 mL of the pharmaceutical suspension. The pH adjusting agent for an embodiment having as an active agent, and including a suspending system having alkaline polymers, such as, sodium carboxymethylcellulose, may be selected from weak organic acids, such as, citric acid, malic acid, glutamic acid, and the like having acceptable taste characteristics for use in taste masked oral suspensions.

Preservatives useful in pharmaceutical suspensions include, but are not limited to, sodium benzoate, potassium sorbate, salts of edetate (also known as salts of ethylenediaminetetraacetic acid, or EDTA, such as, disodium edetate) and parabens (such as, methyl, ethyl, propyl and butyl p-hydroxybenzoic acids esters). The preservatives listed above are exemplary, but each preservative must be evaluated on an empirical basis, in each formulation, to assure the compatibility and efficacy of the preservative. Methods for evaluating the efficacy of preservatives in pharmaceutical formulations are known to those skilled in the art.

The suspensions of the present invention can employ suspending systems as known in the art that include, but are not limited to, at least one thickening component. The thickening component typically includes one or more thickening agents that may be selected from hydrophilic, i.e., water soluble, polymers such as hydrocolloids, swelling or gelling polymers, and the like. In one embodiment, the thickening component combines the attributes of a structuring agent and a swelling agent. In another preferred embodiment, the thickening component combines the attributes of at least two structuring agents, e.g., a primary structuring agent and a secondary structuring agent.

A structuring agent, when introduced into an appropriate aqueous environment, forms an ordered structure, believed to be stabilized by hydrogen bonding and molecular entanglement. Hydrocolloids are a particularly good type of structuring agent. Hydrocolloids are dispersions of particles around which water molecules and solvated ions form a shell-like structure, fluid absorption occurs principally by swelling and enlargement of the structure.

Examples of suitable hydrocolloids include, but are not limited to, alginates, agar, guar gum, locust bean, carrageenan, tara, gum arabic, tragacanth, pectin, xanthan, gellan, maltodextrin, galactomannan, pusstulan, laminarin, scleroglucan, gum arabic, inulin, karaya, whelan, rhamsan, zooglan, methylan, chitin, cyclodextrin, chitosan, cellulosic polymers such as microcrystalline cellulose, carboxymethylcellulose, and derivatives and combinations thereof. In certain embodiments of the present invention, useful structuring agents may be selected from the hydrocolloids xanthan gum, microcrystalline cellulose, carboxymethylcellulose, and derivatives, co-precipitates, and combinations thereof. In one particularly useful embodiment, the thickening component includes xanthan gum as a primary structuring agent and a co-processed combination of microcrystalline cellulose and carboxymethylcellulose (such as that commercially available from FMC as Avicel RC-591) as a secondary structuring agent.

Xanthan gum is a high molecular weight natural carbohydrate, specifically, a polysaccharide. The xanthan gum suitable for use in the present invention is a high molecular weight polysaccharide produced by *Xanthomonas campestris*. Techniques and strains for producing this polysaccharide are described in U.S. Pat. Nos. 4,752,580 and 3,485,719 (the disclosures of which are hereby incorporated by reference). The xanthan gum used in the present invention should have a viscosity in a one percent salt solution of from about 1000 to about 1700 cps (mPa-sec). The one percent solution's viscosity should be measured at 25?C with an LV model Brookfield Synchro-Lectric viscometer at 60 rpm, no. 3 spindle. Xanthan gum is available from several commercial suppliers such a RT Vanderbilt Company and CP Kelco. Examples of suitable xanthan gums are Keltrol, Keltrol F, Keltrol T, Keltrol TF, Xantural 180 and Vanzan NF-ST.

In a useful embodiment, the secondary structuring agent used in the present invention is a dried coprecipitated microcrystal of cellulose and sodium carboxymethylcellulose. Sodium carboxymethyl-cellulose is commonly used as a coprecipitate in microcrystalline cellulose. It is particularly useful if the sodium carboxymethylcellulose is included in the range of from about 8 weight percent to about 19 weight percent of the total weight of the coprecipitated microcrystal of cellulose and sodium carboxymethylcellulose. Useful are microcrystalline cellulose products having in the range from about 8 to about 14 weight percent sodium carboxymethylcellulose. These mixtures as described above are commercially available from a variety of sources, including FMC under the trademark Avicel® CL-611, Avicel® RC-581 and Avicel® RC-591.

The thickening component may optionally include a swelling agent, when exposed to an appropriate aqueous environment, expands and may interact with the structuring agent. Pregelatinized starch is a particularly good swelling agent. Pregelatinized starch, also known as "instantized" starch, is precooked so that it swells and begins to thicken instantly when added to cold water. One particularly suitable pregelatinized starch is prepared from modified, stabilized and waxy, maize food starch, and commercially available from National Starch Company as Instant Starch, Ultrasperse M.

The formulation can be prepared by any of the methods well known in the art of pharmacy. Such methods comprise mixing together the ingredients of the aqueous suspension and include the step of bringing into association the active ingredient with the carrier which constitutes one or more accessory ingredients. In general the formulations are prepared by uniformly and intimately bringing into association the cadotril particles with liquid carriers or finely divided solid carriers or both, and then, if necessary, shaping the product.

In accordance with another subject-matter, the present invention also relates to aqueous suspensions of cadotril particles for use for the treatment and/or prevention of diarrhea, and/or acute gastroenteritis.

As used herein, "stable" refers to a formulation that is substantially free of chemical degradation of racecadotril or substantial color change.

The percent degradation product is determined by calculating the % peak area of the degradation product peak area relative to the peak area of racecadotril in HPLC chromatograms.

Various studies have shown racecadotril to be efficacious in reducing the symptoms of diarrhea. One benefit of using racecadotril over other remedies is that racecadotril has been shown to have fewer side effects such as post-treatment constipation.

Racecadotril has low water solubility, of about 10 micrograms/ml at room temperature.

According to another preferred aspect, said treatment comprises oral administration, preferably one to four times a day.

Examples

The following examples are provided to further illustrate the formulations and methods of the present invention. It should be understood that the present invention is not limited to the examples described.

EXAMPLES

Example 1

Preparation of Particles Containing Racecadotril with a Ratio of Drug: Glyceryl Behenate of 85:15

Approximately 85 g of racecadotril USP (70 μm grade) and 15 g of glyceryl behenate, which is commercially available as Compritol ATO 888, from the Gattefosse corporation in Lyon, France, were added to a suitable vessel while mixing with a laboratory mixer at approximately 50 RPM and heated to above about 75°. The temperature of the solutions can be measured by any means, e.g., using the following: Brand=VWR Digital Thermometer; Model=Traceable; Part Number=61220-601. 400 g of purified water is added to a second suitable stainless steel vessel and heated to approximately 80-90° C. while mixing. The racecadotril and glyceryl behenate mixture is added to the hot water while mixing. The melted mixture of racecadotril, glyceryl behenate and hot water are then added to a separate vessel containing 1000 g of cold water (less than 10° C.) while mixing. The resulting particles were filtered through a 450 mesh stainless steel screen, collected and dried for 6 hours at RT or 25° C. The resulting particles have a mean particle size range between 170 and 250 microns.

Taste. The resulting particles were taste tested in the laboratory for bitterness typically associated with racecadotril. There was substantial reduction in the bitterness.

Figure 2:
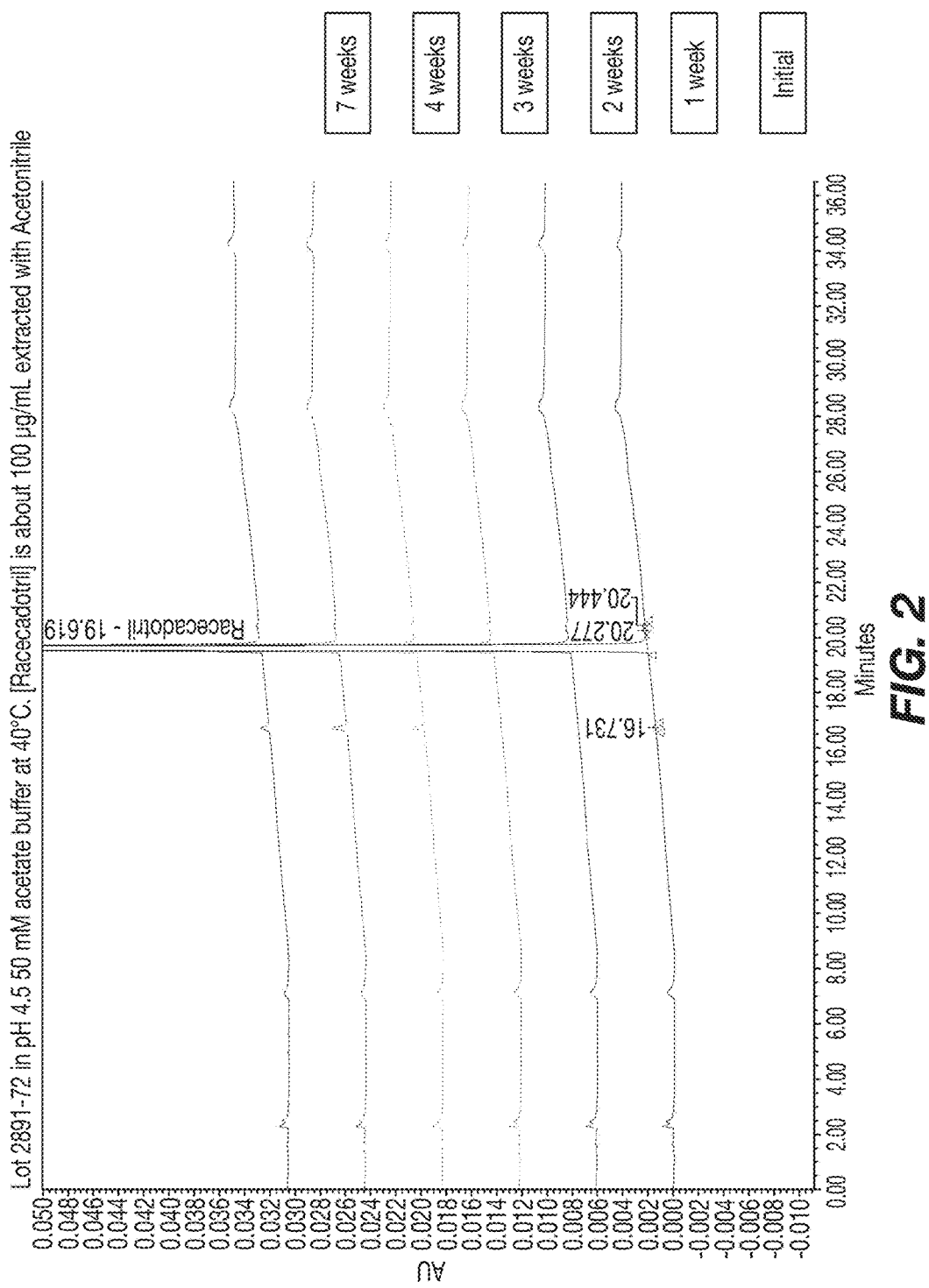
FIG. 2 is a graph showing the degradation profile for racecadotril in a cadotril particle of the invention prepared in accordance with Example 1.

Stability. The resulting particles were suspended in 4.5 pH acetate buffer and were placed in 40° C. oven for 1, 2, 3, 4 and 7 weeks. At the end of seven weeks, samples were analyzed for assay and degradation products. No significant degradation was observed. The results are shown in FIGS. 1 and 2.

Example 2

Preparation of Chewable Tablets Containing Racecadotril

TABLE 3

Preparation of the Tablet Blend Base

| Ingredients | Percent (w/w) | mg/tab | g/batch |
|---|---|---|---|
| Racecadotril (85% active) | 9.8 | 117.6 | 9.8 |
| Dextrose Monohydrate | 83.2 | 998.4 | 83.2 |
| Crospovidone NF | 1.7 | 20.4 | 1.7 |
| Orange Flavor | 0.3 | 3.6 | 0.3 |
| Magnesium Stearate NF | 1.6 | 19.2 | 1.6 |
| Colloidal Silicon Dioxide NF | 0.1 | 1.2 | 0.1 |
| Fumaric Acid NF | 0.6 | 7.2 | 0.6 |
| Citric Acid USP | 0.3 | 3.6 | 0.3 |
| FD&C Yellow 6 Aluminum Lake | 0.2 | 2.4 | 0.2 |
| Acesulfame Potassium | 1.1 | 13.2 | 1.1 |
| Sucralose NF | 1.1 | 13.2 | 1.1 |
| TOTAL | 100.0 | 1200.0 | 100.0 |

The racecadotril particles from Example 1 and the materials in Table 3 were processed using the following procedure: All materials except the racecadotril particles were manually passed through a 30 mesh screen. The materials were placed into a 4 quart V-Blender and mixed for 5 minutes.

Preparation of Chewable Tablets:

To prepare a chewable tablet, the racecadotril particles from Example 1 and the tablet base blend in Table 3 were compressed on a rotary tablet press using ⅝-inch troche-shaped round B-type tooling. The tablets were compressed at a weight of 1400 mg with a hardness range of 4~7 kilopounds.

Example 3

Preparation of Racecadotril Suspension Utilizing Ratio of Racecadotril:Glyceryl Behenate of 85:15

Utilizing the formula in Table 4, an in-situ racecadotril suspension was prepared. First, the racecadotril and glyceryl behenate were melted in a 1000 mL glass beaker A placed in a water bath at 75-85° C. In another 600 mL beaker B, 300 mL DI water (Part I) was heated to 75-85° C. Xanthan gum (Part I) were added to beaker B and mixed until dissolved. Once the racecadotril and the wax were melted in beaker A, the contents of beaker B were poured into beaker A and stirred with a mechanical stirrer 1500-2000 RPM. The temperature of beaker A was maintained at 75-85° C. The water in part II was at room temperature and placed in a third beaker C and cooled down to less than 10° C. Once the racecadotril and the glyceryl behenate formed a uniform dispersion in water, the mixture was removed from the water bath and hotplate. The contents of beaker C were poured into beaker A and slowly and continually stirred at 1000-1500 RPM, as the molten drug and wax mixture congealed into fine particles. The remaining ingredients in Part III were added into beaker A, and mixed for 5 minutes. The resultant suspension was stored in suitable labeled container.

TABLE 4

Formulation for Suspension

| Ingredients | Batch amt (g) |
|---|---|
| Part I | |
| Racecadotril | 20.000 |
| Compritol E ATO | 5.000 |
| Purified Water | 300.000 |
| Xanthan Gum | 1.000 |
| Part II | |
| Purified Water | 478.363 |
| Part III | |
| Acesulfame Potassium | 1.250 |
| Corn Starch | 29.325 |
| Citric Acid | 2.000 |
| Sodium Citrate Dihydrate | 3.087 |
| Sodium Benzoate | 2.500 |
| Sucralose | 0.725 |
| Sucrose | 373.000 |
| Xanthan Gum | 3.750 |
| Total | 1220.000 |

Example 4

Preparation of Particles Containing Racecadotril with a Ratio of Drug: Glyceryl Behenate of 85:15, Alternate Mixing Process Approximately 25 g of racecadotril and 4.41 g of glyceryl behenate, which is commercially available as Compritol ATO 888, from the Gattefosse corporation in Lyon, France, were added to a suitable vessel while mixing with a laboratory mixer at approximately 50 RPM and heated to 80-90° C. 400 g of purified water of water preheated to 80-90° C. is added to the mixture while mixing. 1000 g of cold water (less than 10° C.) is then added to the same vessel while mixing. The resulting particles were filtered through a 450 mesh stainless steel screen, collected and dried for 6 hours at RT or 25° C. The resulting particles have a mean particle size range between 170 and 250 microns.

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims. All patent applications, patents, and other publications cited herein are incorporated by reference in their entirety.

ADDITIONAL REFERENCES

1. Matheson A J, Noble S (April 2000). "Racecadotril". Drugs 59 (4): 829-35; discussion 836-7.
2. (2001) "Racecadotril: an Antidiarrheal Suitable for Use in Infants and Young Children". Drug Ther Perspect 17 (8): 1-5.
3. Salazar-Lindo E, Santisteban-Ponce J, Chea-Woo E, Gutierrez M (2000). "Racecadotril in the treatment of acute watery diarrhea in children". N. Engl. J. Med. 343 (7): 463-7.
4. Spillantini M G, Geppetti P, Fanciullacci M, Michelacci S, Lecomte J M, Sicuteri F (June 1986). "In vivo 'enkephalinase' inhibition by acetorphan in human plasma and CSF". European Journal of Pharmacology 125 (1): 147-50.

What is claimed:

1. A method of manufacturing cadotril particles, comprising:
   melting a cadotril and a wax while mixing to form a mixture consisting of molten cadotril/wax;
   dispersing the molten cadotril/wax mixture in hot water to form a hot dispersion consisting of cadotril, wax and water;
   transferring the hot cadotril/wax/water dispersion into another container containing cold water to form dispersed droplets of cadotril/wax, wherein the dispersed droplets of cadotril/wax congeal and form fine/spherical particles, wherein said fine/spherical particles consist of cadotril and wax; and
   filtering and drying the fine/spherical particles.

2. The method of claim 1, wherein said cadotril is selected from the group consisting of racecadotril, dexecadotril and ecadotril.

3. The method of claim 1, wherein said wax is glyceryl behenate.

4. A method of manufacturing a dosage form, comprising:
   mixing the cadotril particles of claim 1 with dosage form excipients to form a mixture; and
   compressing the mixture into a dosage form.

* * * * *